United States Patent [19]

Blumenthal

[11] Patent Number: 4,914,682
[45] Date of Patent: Apr. 3, 1990

[54] PATIENT TABLE FOR COMPUTERIZED TOMOGRAPHIC SCANNER

[75] Inventor: Rafael Blumenthal, Kiryat Tivon, Israel

[73] Assignee: Elscint, Ltd., Haifa, Israel

[21] Appl. No.: 152,555

[22] Filed: Feb. 5, 1988

[30] Foreign Application Priority Data

Feb. 16, 1987 [IL] Israel .................................... 81581

[51] Int. Cl.⁴ .............................................. A61B 6/04
[52] U.S. Cl. ..................................... 378/20; 378/208; 378/209
[58] Field of Search .......................... 378/20, 208, 209

[56] References Cited

U.S. PATENT DOCUMENTS

| | | | |
|---|---|---|---|
| 4,105,923 | 8/1978 | Hynes, Jr. | 378/20 |
| 4,131,802 | 12/1978 | Braden et al. | 250/363.02 |
| 4,181,858 | 1/1980 | Moore | 378/20 |
| 4,262,204 | 4/1981 | Mirabella | 378/20 |
| 4,576,368 | 3/1986 | Ogawa et al. | |
| 4,583,242 | 4/1986 | Vinegar et al. | |
| 4,613,122 | 9/1986 | Manabe | 378/209 |

*Primary Examiner*—Carolyn E. Fields
*Assistant Examiner*—David P. Porta
*Attorney, Agent, or Firm*—Sandler, Greenblum & Bernstein

[57] ABSTRACT

A patient table for computerized tomographic (CT) scanners located at the rear of the CT gantry to assure more room for CT operators at the front of the gantry. The patient table works in co-operation with a trolley means having a slightly inclined table top holding a stretcher carrying the patient. The stretcher and the patient table include locking means for locking the stretcher to the patient table to enable removing the trolley means from the front of the gantry after the stretcher is locked to the patient table to provide more room at the front of the gantry.

15 Claims, 3 Drawing Sheets

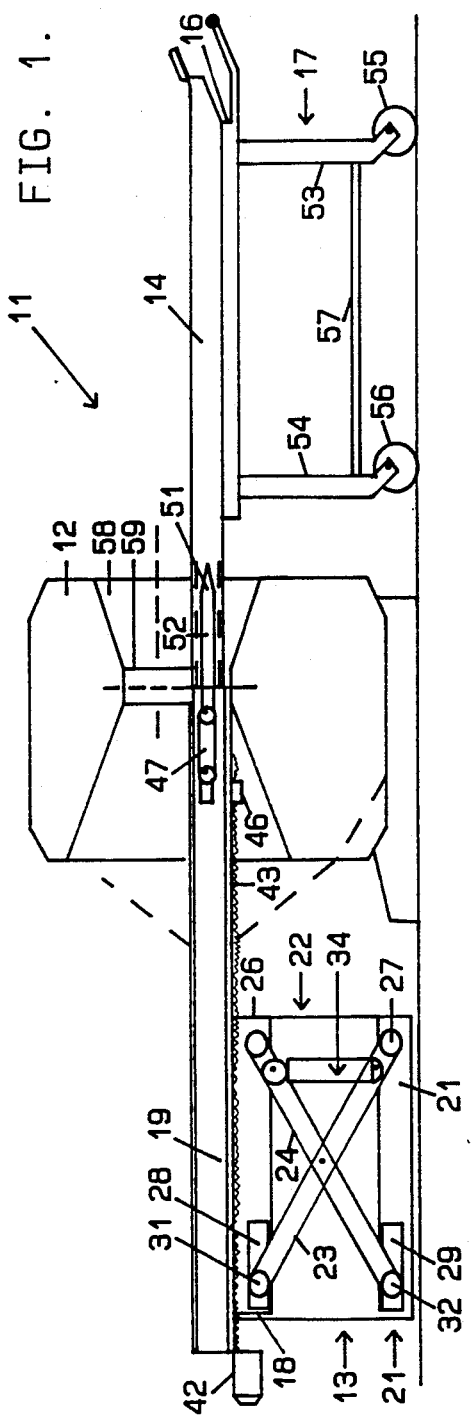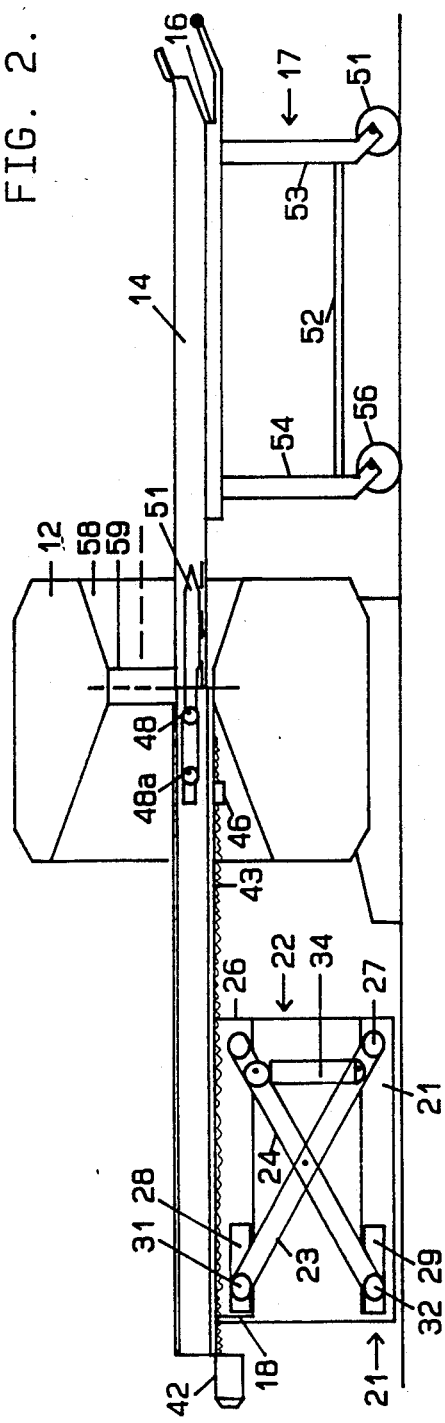

PATIENT TABLE FOR COMPUTERIZED TOMOGRAPHIC SCANNER

FIELD OF THE INVENTION

This invention is concerned with Computerized Tomographic (CT) Imaging Systems and more particularly with a patient table arrangement for such systems.

BACKGROUND OF THE INVENTION

There are many types of patient table arrangements used in conjunction with computerized tomographic equipment and systems, such as, for example, the table mechanism shown in U.S. Pat. No. 4,576,368; or the apparatus for positioning a sample in a computerized axial tomographic scanner which is described in U.S. Pat. No. 4,583,242. All of the known patient table arrangements include some type of support structure on which the patient is inserted into the gantry of the CT scanner for accomplishing the CT scans.

In all of the known arrangements the actual patient support structure remains at the front of the gantry during the scan process. In some systems the distal end of the structure on which the patient rests that is inserted into the gantry is also supported by an auxilliary table at the back of the gantry. In all of the known prior art patient table arrangements the table initially located at the front of the gantry remains at the front of the gantry during the scan This severely limits the working space available at the front of the gantry.

The space limitation makes it difficult for medical personnel to properly administer aid (i.e. oxygen) and/or medication to patients who are under intensive care and require CT scans. Thus, to enhance the ability of the hospital staff t service the intensive care patient being scanned and in general to increase the working space at the entrance to the CT gantry it has long been a desired object to maximize the working space at the front of the gantry.

DESCRIPTION OF THE INVENTION

According to a preferred embodiment of the present invention, a patient table arrangement for CT systems which maximizes the working space at the front of the gantry is provided, said arrangement comprises:
 a stretcher means for supporting a patient during CT scans,
 a stretcher support table located to the rear of the gantry,
 said table comprising;
 guide means extending into said gantry,
 elevator means for varying the height of said guide means,
 attachment means for attaching said stretcher to said stretcher support table,
 means including said guide means extending into the gantry for moving said stretcher means into the gantry from the front of the gantry for the scan while simultaneously removing said attachment means from said gantry to prevent the attachment means from interferring with said CT scans.

According to a feature of the invention the guide means extending into the gantry includes rails or other linear bearing schemes.

According to another feature of the invention, elevator means are provided for varying the height of said guide means.

According to yet another feature of the invention, the means for attaching the guide means to the stretcher comprises:
 plug means mounted to said guide means so as to be movable along said guide means,
 socket means in said stretcher means for receiving said plug means, and
 locking means for locking said plug means to said socket means to lockably attach to said stretcher.

According to another related feature of the invention the plug means are mounted on a carriage which is movable along the guide means.

A further feature of the invention comprises a power screw means affixed to said carriage means, motor means for rotating said power screw means for moving said plug means and consequently said attached stretcher means.

Yet another feature of the invention is that said locking means is a lift and lock means operated by putting said plug means into said socket and elevating said rails. The elevation of the rails with the plug in the socket actuates the locking operation.

A related feature of the invention comprises elevation enable means operated responsive to said plug means being sufficiently within said socket means, and said locked stretcher being cantilevered from said stretcher support table means.

Another feature of the invention includes a special trolley means as part of the patient table arrangement. The trolley means is used to transport the patient from the patients bed to the gantry. The top of the trolley that supports the stretcher has a slight inclination extending towards the distal end of the trolley top away from handles on the trolley. The distal end is the end of the trolley that is juxtaposed to the entrance to the gantry in normal use. The locking means includes a plug locking ramp and a matching socket locking ramp which are not engaged when the plug enters the socket while the stretcher means is supported on the inclined table top of the trolley. However, the socket locking ramp and the plug locking ramp mesh in a locking position when the plug means is entirely within the socket means and the rail means are elevated.

BRIEF DESCRIPTION OF THE DRAWINGS

The above named and other features and objects of the present invention can be best understood when considered in the light of the following description of an exemplary broad aspect of the present invention; wherein:

FIG. 1 is a sectional side view of the inventive patient table arrangement, showing the stretcher support table at the rear gantry and the stretcher support trolley at the front of the gantry;

FIG. 2 is similar to FIG. 1 except that the stretcher and support table are locked together;

GENERAL DESCRIPTION

Figure 3:
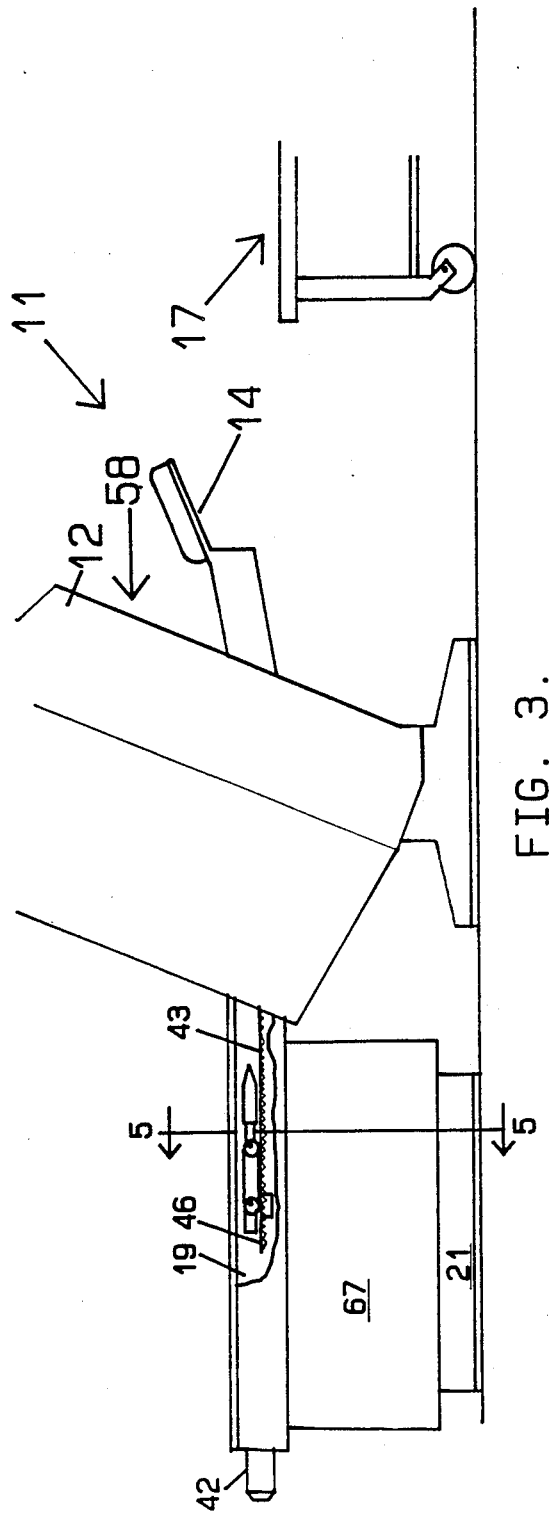
FIG. 3 is a side view of the inventive patient table arrangement with the stretcher within the gantry and the trolley removed from the front of the gantry.

FIG. 1 shows a patient support table arrangement 11 for a CT system comprising a gantry 12. The CT system includes all of the accompanying computer and X-ray equipment (not shown) necessary to operate the gantry to obtain images based on X-ray radiations supplied by an X-ray source and directed to detectors within the gantry after passing through the patient. The patient support table arrangement includes a stretcher support and positioning table 13. The patient is brought to the gantry on a stretcher 14 shown mounted on the table top 16 of a trolley or cart 17. The stretcher support table 13 is shown as having a pair of guide support structures, such as structure 18. A pair of parallel rails or guides, such as guide 19 are preferably integral to the guide support structure.

The table includes a base unit 21 that rests on the floor. Between the base unit and the guide support structures are elevator means for setting the guides 19, 19a at selected heights. More particularly, the elevator means comprises two pairs of longitudinal members, such as members 23, 24 connected between support structure 18 and base "U" section 21a; and longitudinal members 23a, 24a connected between support unit 18a and base "U" section 21b. The ends of the longitudinal members 23, 24 and 23a, 24a closest to the gantry are shown as pivotally attached to the rail support structures 18, 18a with trunions 26, 27 and 26a, 27a. The ends of the longitudinal member 23, 24 and 23a, 24a furthest from to the gantry are connected to slots such as slots 28 and 29 in rail support structure 18 and base "U" section 21, respectively with bearing pins indicated at 31, 32 respectively.

Each pair of longitudinal members are pivotally connected to each other at their longitudinal centers to form "X"s. The oppositely disposed pairs are also connected to each other at their longitudinal centers by transverse rod member 33.

The actual elevating force is supplied by an actuator 34. The actuator may be hydraulically or electrically operated. In a preferred embodiment, the actuator uses an electrically driven and controlled power screw. The actuator comprises body section or cylinder 36 having a power screw 37 controllably extendable therefrom. The body section 36 is coupled to lower transverse rod member 38 which in turn is pivotably connected to longitudinal members 24 and 24a. The actuator power screw 37 is coupled to upper transverse rod member 39 which in turn is pivotably coupled to longitudinal members 23, 23a.

As is readily discernable from the figures when the actuator rod or power screw 37 is extended the ends of the members such as members 23 and 24 move along the slots 28 and 29 toward the gantry and the rail support structure is elevated. When the actuator rod is moved into the cylinder or body 34, the ends of the members 23 and 24 move along slots 28 and 29 away from the gantry and the rail support structure is lowered. Control power is supplied to the actuator over cable 41.

It should be understood that other elevator arrangements can be used within the scope of this invention.

Figure 5:
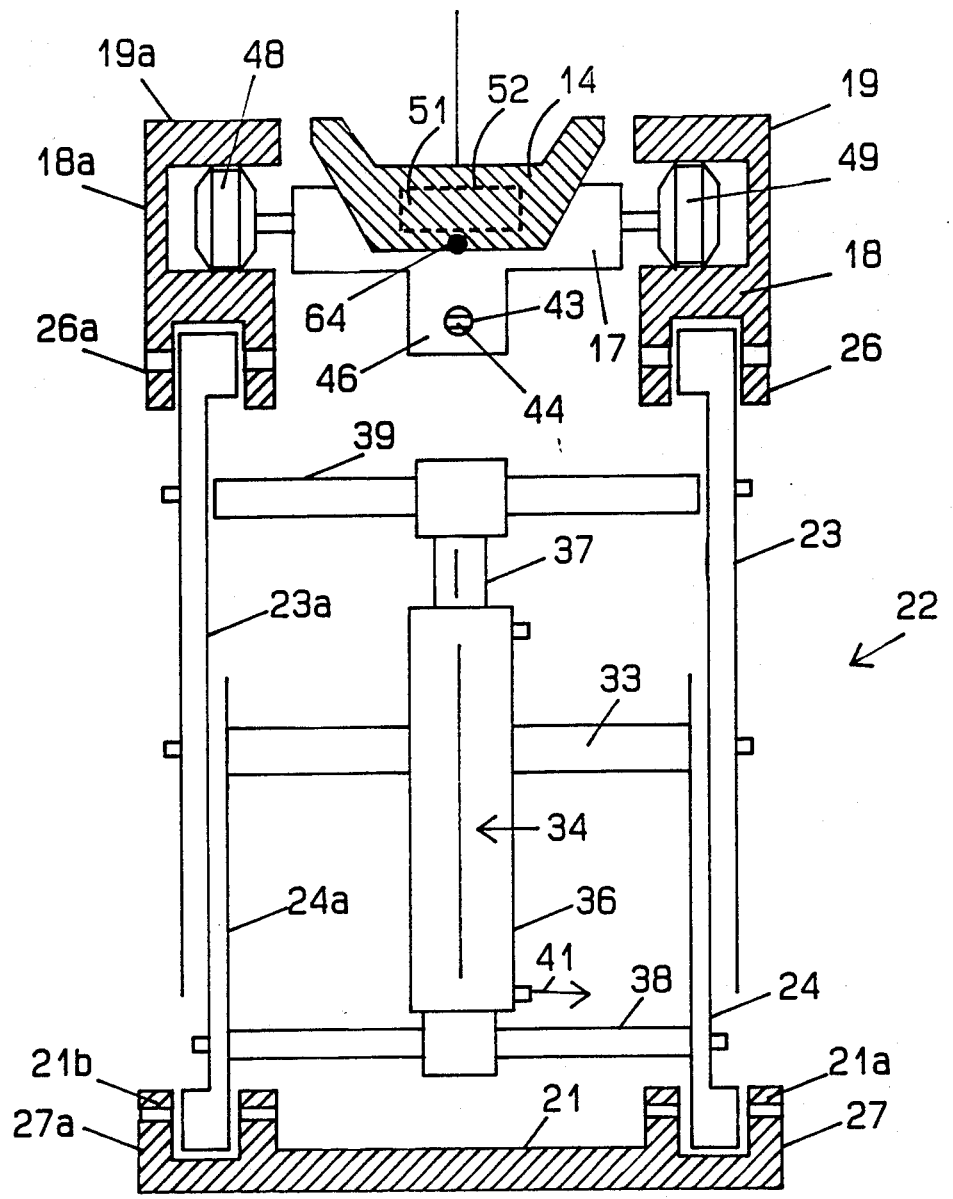
FIG. 5 is a sectional view taken along line 5-5 in FIG. 3 looking in the direction of the arrows.

Means are provided for moving the stretcher 14 horizontally to position it as desired in the gantry. In a preferred embodiment the moving means includes the horizontal guides 19 and 19a. The moving means also include a motor drive means 42. The motor drive rotates a power screw 43. The other end of the power screw 43 is threaded through threaded aperture 44 in brace 46, (FIG. 5). The brace 46 is integrally attached to a carriage unit 47. The carriage unit rides on four wheels such as wheels 48 and 49 in guides 19 and 19a under control of the rotating power screw 43.

The carriage includes means for attaching the carriage 47 to stretcher 14. More particularly, an attaching plug means on the carriage 47 fits into a socket 52 in the stretcher 14.

The trolley 17 other than preferably having a slightly inclined table top is a usual trolley, having legs such as legs 53 and 54 mounted on casters shown at 55 and 56. A platform 57 is shown as included in the trolley for carrying equipment needed by the patient. The platform for example, can be equipped to hold life support systems for the patient in intensive care when that patient is required to undergo a CT scan.

As will be recognised by those skilled in the art, the entrance to the gantry 58 is at the front of the gantry. The rear of the gantry is where the stretcher support table 13 is located in the present arrangement.

The power screw 43 is moved by motor 42 under the control of the operator to thereby move the stretcher 14 between the rails 19, 19a to position the patient as required within the gantry 12. The portion of the patient to be imaged is positioned in the scan circle 59 within the gantry. The scan circle, of course, is made up of the X-ray source spaced apart from the detectors.

These details of the scanning system are not shown but are readily known to those skilled in the art.

Figure 4B:
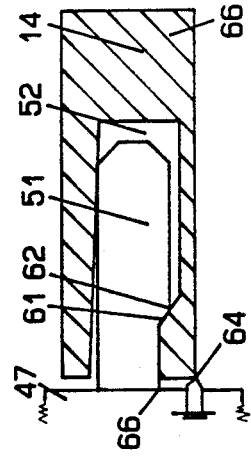
FIG. 4b is a detailed sectional showing of the preferred support table-stretcher locking arrangement in the locked position.
Figure 4A:
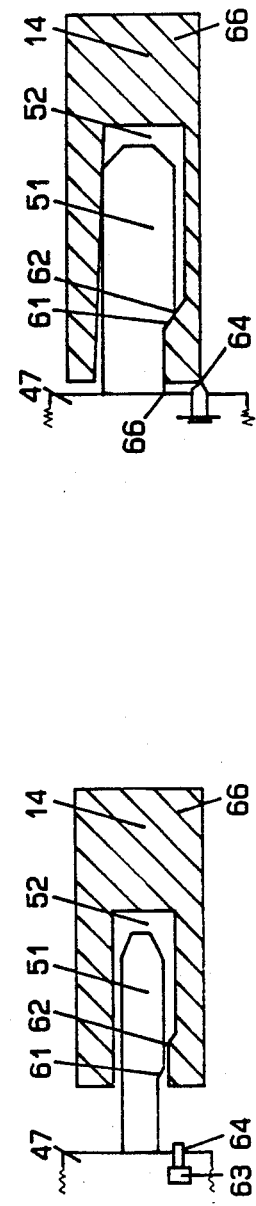
FIG. 4a is a detailed sectional showing of the preferred support table-stretcher locking arrangement in the unlocked position.

Means are provided for locking the plug into the socket. These means are shown in detail in FIGS. 4a and 4b. FIG. 4a shows the plug and the socket in an unlocked state. There, the plug 51 is shown entering the socket 52. The plug is equipped with a plug locking ramp, shown at 61. The socket has a matching socket locking ramp shown at 62. The plug 51 is attached to carriage 47. An elevation enabling switch means 63 is mounted in the carriage 47. A switch actuator 64 extends from the carriage to be accesable for operation when abutted by the end 66 of the stretcher 14. Thus when the plug 51 is properly within the socket 52, the switch actuator 64 is pushed in to operate the switch 63 and enable the elevator actuator 34 of the stretcher support table 13.

Means are provided for normally preventing the locking of the plug to the socket. More particularly there is a slight bias or tilt on the trolley table top 16 so that the stretcher is biased or slanted down towards the gantry entrance 58 at the front of the gantry 12. When the plug is properly inserted into the socket, as shown in FIG. 4b, then the switch actuator 64 causes the switch 63 to operate to enable the elevation of the guide support structure of the stretcher table support at the rear of the gantry. The elevation of the table top, of course, elevates the carriage and plug. The elevation of the plug causes the meshing of the plug locking ramp 61 with the socket locking ramp 62, thereby locking the stretcher to the rails. Unlocking is provided by replacing the stretcher on the inclined top of the trolley and lowering the guide support structures. Subsequently, the motor 42 is operated to move the stretcher 14 between the guides into the gantry until it is placed in the gantry as far as desired. Note that the entire stretcher can be placed in the gantry including the head portion for head scans.

It should be noted that the inventive arrangement described herein is ideally suited for intensive care patients. For example, the head of the patient is the last to enter into the gantry which enables expedient assistance to the patient under intensive care if such assistance is required.

FIG. 3 shows the patient support table arrangement in a side view. Note that the gantry 12 is shown angled. The stretcher 14 is moved between the guides 19 so that most of the stretcher is within the gantry and the patients abdomen section is exposed to the scan.

In FIG. 3 the guide support structure 18 is shown elevated from the skirt walls 67 surrounding the table unit. Thus the elevator mechanism 22 has been operated. The motor means 42 has also been operated. The trolley 17 is removed from the front of the gantry, thereby enabling complete access to the front of the gantry by the personnel operating the system.

In operation, the patient is brought into the CT room on the trolley means. The table unit is at the rear of the CT unit as shown in FIG. 1 with the guides extending into the CT gantry. The trolley unit is manoeouvred so that the stretcher on the top of the trolley with the patient strapped thereto is placed into alignment with the plug means. The plug means enters the socket of the stretcher. In the preferred embodiment the plug is an extended rectangular section having the locking ramp at the end thereof as shown in FIGS. 4a and 4b. The entrance of the plug into the socket is facilitated by the angular inclination of the top of the trolley unit. When the plug is sufficiently within the socket the elevator enable switch is operated and it is possible to elevate the guide support structure 18 lock the carriage to the stretcher.

When the stretcher is locked to the carriage, the motor means 42 is operated. This turns the power screw to move the carriage into a position so that the desired image of the patient will be acquired. When the stretcher 14 is within the gantry the trolley is removed from the front of the gantry Note that in operation it is preferred that the patient's head will be placed into the gantry last; the patient is placed into the gantry feet first. It has been found that with intensive care patients it is much easier to provide aid or medicine to the patient in case of any emergencies when the head is the last to enter the gantry rather then when the feet are the last to enter the gantry. When the head goes into the gantry last then the life support ducts do not cross the scan slice plane.

It should be noted that leg scans can be accomplished when necessary by placing a head support at the distal end of the stretcher and placing the patient into the gantry head first.

Accordingly, a unique patient support table arrangement is provided that enables more efficient patient processing and greater access to the CT gantry.

While the invention has been described with relation to a specific embodiment it should be understood that this description is made by way of example only and not as a limitation on the scope of the invention which is defined by the accompanying claims.

What is claimed is:

1. A patient table arrangement for CT systems including a CT gantry, said gentry having a front side through which a patient is inserted into the gantry and a rear side opposite said front side, said arrangement comprising:
   stretcher means for supporting the patient during scanning,
   cart means for delivering said stretcher means to the front side of said gantry,
   stretcher support means for supporting said stretcher means during scanning independently of any means at the front side of said gantry to leave the front side of said gantry unencumbered.
   said stretcher support means comprising:
   a table unit located to the rear side of said gantry, said table unit comprising:
   guide means extendable into said gantry for supporting said stretcher means independently of any means located at the front side of said gantry and for removing said stretcher means from said cart means to enable the removal of said cart means from the front side of said gantry,
   elevator means for varying the height of said guide means, attaching means for attaching said stretcher means to be supported by and movable on said guide means, and moving means including said guide means and said attaching means for removing said stretcher means into the gantry from the front of the gantry for the scanning for ensuring that said attaching means does not interfere with said scan.

2. The patient, table arrangement of claim 1 wherein said guide means comprises rail means.

3. The patient table arrangement of claim 1 wherein said attaching means comprises lift and lock means.

4. The patient arrangement of claim 1 wherein said elevator means comprises an actuator driven scissors arrangement.

5. The patient table arrangement of claim 4 wherein said actuator driven scissors arrangement comprises:
   actuator means,
   said actuator means comprising a cylinder and extendable rod,
   two-pair of longitudinal members,
   each pair of said two pair of longitudinal members comprising a first longitudinal member and a second longitudinal member,
   said table unit further comprising:
   base means and a guide support structure,
   said first longitudinal member extending from the side of the base means closest to the gantry to the side of the guide support structure furthest from the gantry,
   said second longitudinal member extending from the side of the guide support structure closest to the gantry to the side of the base means furthest from the gantry,
   first trunion means for connecting said first longitudinal member to the base means,
   second trunion means for connecting said second longitudinal member to the guide support structure, first bearing slot means at the side of said base means closest to said gantry, second slot means at the side of said rail support structure closest to said gantry,
   first bearing pin means for attaching said first longitudinal member to the base means through said first slot means,
   second bearing pin means for connecting said second longitudinal member to the rail support structure at the second slot means,
   an upper transverse rod member connected between the first longitudinal member of said first pair of longitudinal members and said first longitudinal members of said second pair of longitudinal members, a lower transverse rod member connected between the second longitudinal member of the first pair of longitudinal members and the second longitudinal member of said second pair of longitudinal members, a middle transverse rod member connected between the first and second pair of longitudinal members at the intersections of the first and second longitudinal members in each of said first and second pair of longitudinal members, means for connecting said actuator means between said upper and lower transverse rod members, with means for connecting the body of the actuator means to the lower transverse rod member, means for connecting the extensible rod of the actuator to the upper transverse rod member, whereby when the actuator rod is extended said guide support structure is elevated and the ends of said first and second longitudinal members slide horizontally along the slots away from said gantry and when said actuator rod member is moved into the cylinder of the actuator then the rail support structure is lowered and the ends of the first and second longitudinal members move horizontally along the slots toward said gantry.

6. A patient table arrangement for CT systems including a CT gantry, said arrangement comprising:

stretcher means for supporting a patient during scans, trolley means for delivering said stretcher means to the front of said gantry, said trolley means comprising:

a table top having an inclination extending longitudinally from handles on one side of the trolley means to the other side of said trolley means, said other side of said trolley means being the side which is normally placed juxtaposed to the entrance to the gantry, a table unit located at the rear of the gentry, said table unit comprising:

guide means extendable into said gantry, elevator means for varying the height of said guide means, attaching means for attaching said stretcher means to be movable on said guide means, said attaching means including carriage means movably mounted to said guide means, and, moving means for moving said carriage means along said guide means to move said stretcher means into the gantry from the front of the gantry for the scan and assuring that the said attaching means does not interfere with said scan.

7. The patient table arrangement of claim 6 wherein said attaching means for said stretcher means to be movable on said guide means includes carriage means movably mounted to said guide means, and said moving means including means for moving said carriage means along said guide means.

8. The patient table arrangement of claim 7 wherein said means for moving said carriage means comprises motor means, said motor means rotating a threaded rod means, threaded aperture means for connecting said threaded rod to said carriage means to thereby move said carriage means when the threaded rod rotates.

9. The patient table arrangement of claim 7 wherein said attaching means comprises lift and lock means, said lift and lock means comprising:

plug means attached to said carriage means, socket means in said stretcher means for receiving said plug means, said plug and socket means each including locking means for locking said plug and socket means together, said locking means comprising socket ramp locking means and plug ramp locking means, said locking means being normally unlocked after insertion of said plug means into said socket means because of the incline of said trolley table top.

10. The patient table arrangement of claim 7 including a lift and lock means comprising:

plug means attached to said carriage means, and socket means in said stretcher means for receiving said plug means, 11. The patient table arrangement of claim 10 wherein said plug and socket means each include locking means for locking said plug and socket means together.

12. The locking means of the patient table arrangement of claim 9 wherein said locking means further includes elevator enabling means.

13. The patient table arrangement of claim 12 wherein said elevator enabling means comprises switch means located in said carriage means, said switch means having actuator means extending from said carriage means exposed to being abutted by the end of said stretcher means when said plug means is properly within said socket means.

14. The patient table arrangement of claim 13 wherein said socket ramp locking means and said plug ramp locking means mesh responsive to the elevation of said guide means enabling said stretcher to be lockingly cantilevered from the end of said guide means.

15. A patient table arrangement for CT systems including a CT gantry having a front side for receiving a patient therein and a back side that is opposite to said front side, said arrangement comprising:

stretcher means for supporting the patient during scans, removable trolley means for use in inserting said stretcher means into the CT gantry from the front side thereof, a table unit located at the rear side of said gantry, and said table unit comprising attachment means for supporting and controlling the horizontal and vertical position of said stretcher means independently of any equipment at the front side of said gantry during the scan enabling the removal of said trolley means leaving the front of said gantry unencumbered.

* * * * *